United States Patent [19]

Besson

[11] Patent Number: 4,981,619

[45] Date of Patent: Jan. 1, 1991

[54] PROCESS FOR PREPARING ALPHA-HYDROXY ACIDS

[75] Inventor: Bernard Besson, Villeurbanne, France

[73] Assignee: Rhone Poulenc Specialities Chimiques, Courbevoie, France

[21] Appl. No.: 935,850

[22] Filed: Nov. 28, 1986

[30] Foreign Application Priority Data

Nov. 27, 1985 [FR] France .................... 85 17748

[51] Int. Cl.$^5$ .................... C07C 51/10; C07C 59/01
[52] U.S. Cl. .................... 260/413; 260/410.9 R; 558/353; 560/232; 562/406; 562/497; 562/520
[58] Field of Search .................... 260/413; 560/232; 562/520, 406, 497

[56] References Cited

FOREIGN PATENT DOCUMENTS

WO84/02699  7/1984  PCT Int'l Appl. .
2026478     2/1980  United Kingdom ............ 562/520

*Primary Examiner*—Vivian Garner
*Attorney, Agent, or Firm*—Finnegan, Henderson, Farabow, Garrett, & Dunner

[57] ABSTRACT

A process for preparing alpha-hydroxycarboxylic acids. An organic halide is reacted with carbon monoxide and a hydrogen donor compound, in the presence of a carbonylation catalyst and an inorganic base, at a temperature of at least 90° C.

13 Claims, No Drawings

PROCESS FOR PREPARING ALPHA-HYDROXY ACIDS

BACKGROUND OF THE INVENTION

The present invention relates to a process for preparing alpha-hydroxycarboxylic acids by a reductive double carbonylation of organic halides.

Alpha-hydroxycarboxylic acids, such as lactic acid, alpha-hydroxybutyric acid and alpha-hydroxyoctanoic acid, are important industrial products. They are used either directly (for example in the foodstuffs field, in the case of lactic acid), or as intermediates in organic synthesis.

There are various access routes to alpha-hydroxy acids. The most advantageous from the industrial standpoint are (1) fermentation (preparation of lactic and alpha-hydroxybutyric acids, in particular), (2) hydrolysis of alpha-halocarboxylic acids in alkaline medium and (3) acid hydrolysis of aldehyde cyanohydrins (alpha-hydroxynitriles).

Regardless of the value of these various processes, they are limited by certain disadvantages. Thus, fermentation processes are not of general use, and lead to complex mixtures from which the recovery of the alpha-hydroxy acid sought proves complicated. The organic synthesis processes involve the preparation of starting substances by carrying out multi-stage methods (preparation of alpha-halo acids or alpha-hydroxynitriles, for example).

For all these reasons, the industry continues to seek processes for preparing alpha-hydroxy acids employing readily accessible reagents. The present invention relates to such a process.

More specifically, the present invention is a process for preparing alpha-hydroxycarboxylic acids, comprising the step of reacting an organic halide with carbon monoxide and a hydrogen donor compound, in the presence of a carbonylation catalyst and an inorganic base, at a temperature of at least 90° C.

DETAILED DESCRIPTION

A representative organic halide is any compound containing a radical of the formula:

(in which X denotes a halogen atom), either linked to a linear or branched alkyl radical, which alkyl radical may or may not be substituted with functional radicals or with cycloalkyl, aryl, aryloxy or heterocyclic radicals, or linked to an aryloxy radical. One skilled in the art can readily obtain or synthesize a suitable organic halide.

The term "lower alkyl and lower alkoxy radicals" is defined herein to include linear or branched alkyl or alkyloxy radicals containing 1 to 4 carbon atoms.

The production of alpha-hydroxy acids by reaction of carbon monoxide with an organic halide and a hydrogen donor compound, in the presence of a carbonylation catalyst, at a temperature of at least 90° C., is a result which is completely unexpected in view of the prior art. In effect, in the international patent application published under No. WO 84/02,699, a process was described for preparing alpha-ketocarboxylic acids by double carbonylation of an organic halide, selected from the group consisting of alkyl halides and phenoxyalkyl or phenylalkyl halides in which the phenyl radical is at least in the alpha-position with respect to the carbon atom bearing the halogen atom, in an aqueous organic medium and in the presence of a carbonylation catalyst.

This international patent application teaches that alpha-ketocarboxylic acids are preponderantly obtained, regardless of the conditions employed and, in particular, regardless of the solvents used (primary, secondary or tertiary alcohols) and the temperature employed (from 30° to 150° C.). For those skilled in the art, it is surprising that, by performing the reaction of an organic halide at a temperature of at least 90° C. and in the presence of a hydrogen donor compound, an alpha-hydroxy acid is formed preponderantly instead of an alpha-keto acid.

Preferably, the subject of the present invention is a process for preparing alpha-hydroxycarboxylic acids of the formula:

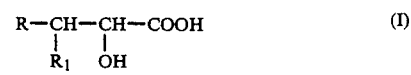

in which R and $R_1$, which may be identical or different, denote:

a hydrogen atom;

an aryloxy radical; or a linear or branched alkyl radical containing from 1 to 20 carbon atoms. The linear or branched alkyl radical may be substituted with one or more radicals selected from the group consisting of:

(a) one or more functional radicals which are inert under the conditions of the reaction, such as nitro, nitrile, alkylcarbonyloxy;

(b) one or more aryl radicals;

(c) one or more cycloalkyl radicals;

(d) one or more heterocyclic radicals containing one or more hetero atoms selected from the group consisting of oxygen, nitrogen, and sulphur; and (e) an aryloxy radical.

Preferably, in the formula (I), R and $R_1$ independently denote:

(a) an alkyl radical such as methyl, ethyl, n-propyl, isopropyl, n-butyl, isobutyl, sec-butyl, t-butyl, n-pentyl, isopentyl, n-hexyl, n-heptyl, n-octyl, 2-ethylhexyl, n-dodecyl, n-hexadecyl, and n-nonadecyl;

(b) an alkyl radical substituted with an aryl radical, i.e., an arylalkyl radical, containing from 1 to 20 carbon atoms in the alkyl portion and 1 or 2 fused or unfused benzene rings in the aryl portion, it being possible for the benzene rings to be substituted with one or more linear or branched alkyl radicals containing from 1 to 4 carbon atoms, one or more alkoxy radicals containing from 1 to 4 carbon atoms, one or more halogen (chlorine, bromine, fluorine) atoms, and one or more nitrile, nitro, or alkylcarbonyloxy groups. Preferably, R and $R_1$ independently denote an arylalkyl radical of the formula:

in which: Ar denotes an aryl radical containing one or two fused or unfused benzene rings; - R' denotes one or more substituents selected from the group consisting of an alkyl radical containing from 1 to 4 carbon atoms, an alkoxy radical containing from 1 to 4 carbon atoms, a halogen atom, a nitrile group, a nitre group, an alkylcarbonyloxy group: n denotes an integer from 0 to 3 when Ar contains a single benzene ring or from 0 to 5 when Ar contains two benzene rings; and m denotes an integer from 1 to 20, preferably from 1 to 10.

(c) an aryloxyalkyl radical containing from 1 to 20 carbon atoms in the alkyl portion and 1 or 2 fused or unfused benzene rings in the aryl portion, it being possible for the benzene rings to be substituted with one or more linear or branched alkyl radicals containing from 1 to 4 carbon atoms, alkoxy radicals containing from 1 to 4 carbon atoms, one or more halogen (chlorine, bromine, fluorine) atoms, and one or more nitrile, nitro, or alkylcarbonyloxy groups. In this case, R and/or $R_1$ preferably denote an aryloxyalkyl radical of the formula:

$$(R')_n-Ar-O-(CH_2)-_m \qquad (III)$$

in which R', Ar, n and m have the definition given above; and (d) an aryloxy radical containing one or two fused or unfused benzene rings, of the formula:

$$(R')_n-Ar-O- \qquad (IV)$$

in which R', n and Ar have the meaning given above. Examples of aryloxy radicals include phenoxy, o-methylphenoxy, o-methoxyphenoxy, 2,4-dimethylphenoxy and naphthyloxy radicals.

Specific examples of the arylalkyl and aryloxyalkyl radicals referred to above include benzyl, 1-phenylethyl, 2-phenylethyl, 3-phenylpropyl, 2-phenylpropyl, 4-phenylbutyl, ortho-tolymethyl, xylylmethyl, ortho-methoxyphenylmethyl, p-chlorophenylmethyl, 2-naphthyl-methyl, phenyloxymethyl, 2-phenyloxyethyl and 2-phenoxy-propyl radicals.

In the formula (I), $R_1$ preferably denotes a hydrogen atom or a lower alkyl radical.

Examples of alpha-hydroxy acids which can be prepared by the process according to the present invention include lactic acid; alpha-hydroxybutyric acid; 2-hydroxy-4-methylpentanoic acid; alpha-hydroxypentanoic acid;. 2-hydroxy-3,3-dimethyl-butanoic acid; alpha-hydroxyoctanoic acid; 2-hydroxydecanoic acid; 2-hydroxypalmitic acid; 2-hydroxystearic acid; and 4-phenyl-2-hydroxybutanoic acid.

Preferred organic halides used as starting substances in the process according to the present invention can be represented by the formula:

$$R-CH-X \atop R_1 \qquad (V)$$

in which R and $R_1$ have the meaning given earlier with respect to formula (I) and X denotes a halogen atom and preferably a chlorine or bromine atom.

Examples of organic halides of formula (V) include methyl chloride and bromide, chloroethane, 1-chloropropane, 2-chloropropane, 2-bromopropane, 1-chlorobutane, 2-chlorobutane, isobutyl chloride, isobutyl bromide, 1-chloropentane, 1-bromohexane, 1-bromooctane, 1-chlorooctadecane, phenethyl chloride and bromide, 2-(ortho-methylphenyl)ethyl chloride, 2-(2,4-di-methylphenyl)ethyl bromide, 3-phenylpropyl chloride, 4-phenylbutyl bromide, phenoxymethyl chloride, 2-phenoxyethyl bromide, 3-phenoxypropyl chloride and 4-phenoxybutyl chloride.

Hydrogen donor compounds suitable for the formation of an alpha-hydroxy acid include any organic compound containing hydrogen atoms which are labile under the conditions of the reaction, that is to say, are labile in the presence of carbon monoxide, an inorganic base and a carbonylation catalyst, and are labile at the reaction temperature. A preferred class of hydrogen donors consists of saturated primary and secondary aliphatic alcohols.

More specifically, there are used alcohols of the formula:

$$R_2-CHOH-R_3 \qquad (VI)$$

in which $R_2$ denotes a hydrocarbon radical containing from 1 to 20 carbon atoms and $R_3$ denotes a hydrogen atom or a hydrocarbon radical identical to or different from $R_2$. In the formula (VI), $R_2$ and/or $R_3$ denotes, more especially, alkyl, arylalkyl, aryl, alkylaryl or cycloalkyl radicals. Examples of the radicals $R_2$ and $R_3$ include methyl, ethyl, n-propyl, sec-butyl, cyclohexyl, phenyl, benzyl, xylyl and tolyl radicals.

Alcohols such as methanol, ethanol, 1-propanol, isopropanol, isobutanol, 2,2-dimethyl-1-propanol, 2-butanol, 3-methyl-1-butanol and isopentanol may be mentioned by way of non-limitative examples of alcohols of the formula (VI). The secondary alcohols are preferably used.

Without the invention being limited in any way whatsoever to a particular reaction mechanism, it may be represented by the following reaction scheme when the hydrogen donor is an alcohol;

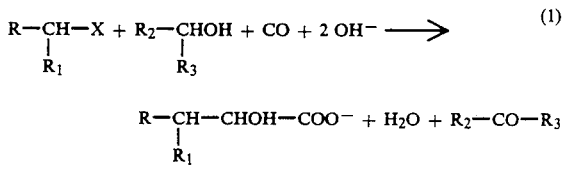

$$R-CH-X + R_2-CHOH + CO + 2 OH^- \longrightarrow \atop R_1 \qquad R_3 \qquad (1)$$

$$R-CH-CHOH-COO^- + H_2O + R_2-CO-R_3 \atop R_1$$

in which R, $R_1$, $R_2$, $R_3$ and X have the meaning given before for R, $R_1$, $R_2$, or $R_3$.

The amount of hydrogen donor, expressed in the mole per mole of organic halide, can vary within wide limits, depending on the nature of the donor. The amount is preferably at least equal to 1 mole per mole of organic halide, and still more preferably at least equal to 5 moles per mole.

There is no critical upper limit to the amount of hydrogen donor, and a large excess of the latter may be employed. When it is a liquid under the conditions of the reaction, the hydrogen donor can advantageously be used as the reaction medium. Without departing from the scope of the present invention, it will be possible to employ less than 1 mole of hydrogen donor per mole of halide, although an insufficient amount of donor would, of course, result in an incomplete conversion of the halide.

The inorganic base used to perform the reaction is preferably chosen from the alkali metal hydroxides, such as sodium hydroxide, potassium hydroxide or lithium hydroxide, or the alkaline earth metal hydroxides such as $Ba(OH)_2$, $Ca(OH)_2$ or $Mg(OH)_2$, or the alkali metal or alkaline earth metal carbonates. LiOH or Ca(OH)$_2$ are preferably used.

The amount of inorganic base can vary within wide limits. In general, the amount of base used is in the region of 1 mole per mole of organic halide. However, it is possible to work with an excess of base, which can, for example, reach one mole or more per mole of halide, without departing from the scope of the present invention.

The reaction is preferably performed in the presence of a larger amount of base, such as from 1.1:1 to 4:1 moles per mole of halide.

As a catalyst, it is possible to use any metal compound known for initiating carbonylation or double carbonylation reactions, such as those mentioned in French Patent No. 74/00,533; the French patent application published under No. 2,429,772; or the international patent application published under the number WO 84/02,699. The disclosures of these documents relating to such catalysts are specifically incorporated by reference herein.

Metal carbonyls are preferably used as catalysts and especially the iron, nickel and cobalt derivatives. It is possible to use metal carbonyls such as iron pentacarbonyl, nickel tetracarbonyl, dicobalt octacarbonyl, tetracobalt dodecacarbonyl and alkali metal or alkaline earth metal salts of metal carbonyl hydrides and more preferably alkali metal or alkaline earth metal tetracarbonylcobaltates(1-). It is also possible, without departing from the scope of the present invention, to use carbonyl complexes of iron, nickel and cobalt with mono- or polydentate ligands. Carbonyl derivatives of cobalt constitute an especially preferred class of catalysts.

The amount of catalysts, expressed as gram-atoms of metal per mole of organic halide, can preferably be from about 0.0001:1 to 1:1. More preferably, this amount is chosen so that the above ratio is from 0.001:1 to 0.4:1.

Although the hydrogen donor may be used as the reaction medium, as has been stated before, it can prove advantageous to work in the presence of a dissolving intermediary which is inert under the conditions of the reaction. In this case, use is preferably made of water or a tertiary alcohol such as t-butanol, t-amyl alcohol, 2-methyl-2-pentanol or 2,3-dimethyl-2-butanol, or an ether such as dioxane, tetrahydrofuran, 1,2-dimethoxyethane or diglyme.

It is possible, without departing from the scope of the present invention, to use a mixture of at least two inert solvents; from this standpoint, the use of mixtures of water with water-miscible organic solvents is most especially suitable. Thus, it is possible to use water/t-butanol, water/dioxane or water/tetrahydrofuran mixtures.

The concentration of the organic halide in the reaction medium is not critical. It is preferable that it should be sufficient to provide for as high a productivity as possible for the apparatus. One skilled in the art can readily ascertain a proper concentration of organic-halide for specific reaction conditions.

The pressure of carbon monoxide at which the reaction is performed can vary within wide limits. In general, it can assume any value ranging from about 1 to 200 bars, and preferably from 5 to 150 bars.

To direct the reaction towards the preponderant formation of alpha-hydroxy acid, the temperature used must be at least equal to 90° C. It has been found that above this temperature, the yield of alpha-hydroxy acid increases with the temperature up to an optimal value of the latter, which depends on the nature of the substrate. Above this readily determinable optimal value, the yields of alpha-hydroxy acids decrease as the temperature rises.

In general, it is preferable to work at a temperature of less than 160° C. A temperature value ranging from about 90 to 130° C. is most especially suitable.

From a practical standpoint, the process according to the invention is especially simple to carry out. It suffices, in effect, to charge a reaction apparatus with the organic halide, the hydrogen donor, water and/or inert organic solvent if desired, the catalyst and the base, to then introduce a sufficient amount of carbon monoxide at the appropriate pressure and to then bring the reactants to the chosen temperature with agitation. At the end of the reaction, the alpha-hydroxy acid is present in the form of its alkali metal or alkaline earth metal salt and can be recovered by the usual means, which are well-known to those skilled in the art.

When the salt obtained is in solution in the reaction medium, it is possible to precipitate it by any suitable means and then to separate it by filtration. When the salt formed is insoluble or partially insoluble, it is filtered off. In all cases, the alpha-hydroxy acid can be liberated by acidification using an aqueous solution of an inorganic acid, and then recovered by extraction with a solvent.

The process according to the invention is especially well adapted to operation in continuous fashion.

The examples which follow illustrate the invention and show how it may be put into practice.

EXAMPLE 1

The following are introduced into a 125-ml stainless steel autoclave purged beforehand with argon:

| | |
|---|---|
| 1-bromooctane: | 79 mmol (15.3 g) |
| lime: | 123 mmol (9.1 g) |
| water: | 11.7 g |
| isopropanol: | 46 g |
| $Co_2(CO)_8$ | 1.15 mmol (393 mg). |

The autoclave is hermetically sealed and placed in an oven agitated by shaking and connected to a system for feeding gas under pressure. A pressure of 20 bars of CO is admitted in the cold and the autoclave is then heated to a temperature of 120° C. When this temperature is reached, the pressure is adjusted to 90 bars. After 2 h 50 min, the autoclave is cooled and the pressure released. After the autoclave is opened, the reaction mass is filtered.

There are obtained a solid white product (13.1 g), and an aqueous alcoholic solution. In the solid product, lime (2.4 g), 0.4 g of the calcium salt of nonanoic acid and 10.2 of the calcium salt of alpha-hydroxydecanoic acid are shown to be present. The yield of acid relative to the 1-bromooctane charged, as alpha-hydroxydecanoic acid (in the form of Ca salt) is 65% (actual yield or AY).

The identification of the different products formed during the reaction, and present in the different phases of the reaction mass, is performed by gas chromatography or by high pressure liquid chromatography, depending on the case, by comparison with appropriately characterized samples. In the solid product, lime, the calcium salt of nonanoic arid and the calcium salt of alpha-hydroxydecanoic acid are shown to be present. The calcium salt of alpha-ketodecanoic acid is not observed, either in the solid or in the aqueous alcoholic solution.

COMPARATIVE EXAMPLE A

The procedure is the same and the charges by weight are the same as in Example 1, except that the temperature is 70° C. and the reaction time 16 hours.

In the solid product (12.6 g), only lime, nonanoic acid and alpha-ketodecanoic acid in the form of Ca salt are observed, but no alpha-hydroxydecanoic acid. The alpha-ketodecanoic acid is obtained in a 35% yield.

COMPARATIVE EXAMPLE B

The procedure is the same and the charges by weight are the same as in Example 1, except that isopropanol is replaced by tert-butanol.

In the soluble product, only lime, nonanoic acid and alpha-ketodecanoic acid in the form of Ca salt are observed, but not alpha-hydroxydecanoic acid. The alpha-ketodecanoic acid is obtained in a 56% yield.

EXAMPLE 2

The procedure is the same and the charges are the same as in Example 1, except that 1-bromooctane is replaced by 1-bromo-2-methylpropane in the same molar amounts, and the pressure is only 60 bars and the time is 18 hours.

In the solid (11.1 g), only lime and the Ca salt of 4-methyl-2-hydroxypentanoic acid (9.4 g) are assayed. The corresponding alpha-keto acid is observed only in the form of traces. The yield of 2-hydroxy-4-methylpentanoic acid is 80%. In addition, in the mother liquors, 6 mmol of 3-methylbutanoic acid are assayed in the form of its calcium salt.

COMPARATIVE EXPERIMENT C

The procedure is as in Example 2, except that the temperature is 70° C. and the reaction time 18 hours. In the solid, alpha-hydroxy acid is not observed, but only the corresponding alpha-keto acid in the form of Ca salt, in a 10% yield.

COMPARATIVE EXPERIMENT D

The procedure is as in Example 2, except that isopropanol is replaced by tert-butanol, the reaction time is 6 hours and the pressure is 90 bars. In the solid, keto acid (yield 37%) and monocarbonylation acid (yield 57%) are assayed in the form of their Ca salt.

EXAMPLE 3

The procedure, is as in Example 1, except that the substrate introduced is 1-bromo-2-methylpropane, the pressure is 60 bars and the reaction time is 18 hours and 30 minutes. The reagents are introduced in the same mole ratio as in Example 1. After filtration of the reaction mass, 10.8 g of solid are recovered, in which 3.5 g of lime and 37 mmol of 4-methyl-2-hydroxypentanoic acid in the form of calcium salt are assayed after analysis. 4-methyl-2-oxopentanoic acid is not observed in the form of calcium salt, either in the mother liquors or in the solid. The yield of alpha-hydroxy acid is 47%.

EXAMPLE 4

The procedure is as in Example 3, except that the temperature is only 110° C. and the reaction time is 5 hours 30 minutes. The substrate is phenethyl bromide. The reagents are introduced in the same mole ratios. After the reaction has stopped, the autoclave is cooled and then outgassed; the reaction mass is filtered and the sold product obtained is rinsed with water. 197.5 g of aqueous alcoholic solution and 15.6 g of solid product are obtained. Analysis of the aqueous alcoholic phase shows that all the phenenthyl bromide has been consumed. The aqueous alcoholic solution is then concentrated to dryness; 6.2 g of dry extract is obtained, and this is ground with the solid product. The solid thereby obtained is analyzed by potentiometry and high pressure liquid chromatography. The following composition is obtained:

$Ca(OH)_2$: 40.9 mmol (3.03 g);
$CaBr_2$: 42 mmol (4.20 g);
calcium salt of 4-phenyl-2-oxobutanoic acid: 2.6 acid meq (0.51 g);
calcium salt of 4-phenyl-2-hydroxybutanoic acid: 66.6 acid meq (13.25 g);
calcium salt of 3-phenylpropanoic acid: 4.9 acid meq (0.8 g).

The yield of calcium salt cf 4-phenyl-2-hydroxybutanoic acid is 84% relative to the phenethyl bromide.

EXAMPLE 5

The procedure is the same as in Example 3, except that the reaction temperature is 155° C. and the reaction time is 4 hours. After filtration of the reaction mass, 9.9 g of solid product and a filtrate of 46.9 g are recovered. In the solid product, 9 mmol of 4-methyl-2-hydroxypentanoic acid in the form of calcium salt are assayed exclusively. In the aqueous alcoholic solution, 18 mmol of 4-methyl-2-hydroxypentanoic acid is assayed, to the exclusion of other carbonylation products.

EXAMPLE 6

The procedure is the same as in Example 3, except that the reaction temperature is 90° C. and the time is 19 hours 15 minutes. After filtration of the reaction mass, 8.9 g of solid product and 64.2 g of aqueous alcoholic solution are recovered. In the solid product, 0.2 mmol of 4-methyl-2-oxopentanoic acid, 16.6 mmol of 4-methyl-2-hydroxypentanoic acid and 1.5 mmol of 3-methylbutanoic acid are assayed in the form of their calcium salt. In the aqueous alcoholic solution, 8.8 mmol of 3-methylbutanoic acid are assayed.

EXAMPLE 7

The procedure is the same as in Example 3, except that isopropanol is replaced by a mixture of tert-butanol and ethanol in the respective amounts of 36.7 g and 9.2 g. The reaction time is 6 hours and 20 minutes, and the other conditions are unaltered. After filtration of the reaction mass, 41.7 g of aqueous alcoholic solution and 6.40 g of solid products are recovered. The analyses show that, in the solid, there are 1.5 mmol of 4-methyl-2-oxopentanoic acid and 12.8 mmol of 4-methyl-2-hydroxypentanoic acid in the form of calcium salt. In the aqueous alcoholic solution, only 10 mmol of 4-methyl-2-hydroxypentanoic acid are assayed in the form of calcium salt.

EXAMPLE 8

The procedure is the same, the substrate is the same and the charges are the same as in Example 2, except that the pressure is 40 bars and the reaction time is 14 hours 30 minutes. After cooling of the autoclave and outgassing, the reaction mass is filtered. Assay of the aqueous alcoholic solution (filtrate) shows that the substrate has been completely converted. The filtrate is concentrated to dryness; 16.8 g of residue are obtained.

This residue is mixed with the solid obtained by filtration (5.75 g) and homogenized. The solid thereby obtained is analyzed and the following products are assayed:

Ca(OH)$_2$: 3.41 g;

4-methyl-2-hydroxypentanoic acid (Ca salt): 69.8 mmol (10.5 g); and isovaleric acid (Ca salt): 9.1 mmol (1.0 g).

The yield of 4-methyl-2-hydroxypentanoic acid in the form of calcium salt is 88.4%.

What is claimed is:

1. A process for preponderantly preparing, relative to an alpha-ketocarboxylic acid, an alpha-hydroxycarboxylic acid comprising the setup of reacting an organic halide of the formula

   (V)

wherein R and R$_1$, which may be identical or different, are hydrogen, alkyl of 1-20 carbon atoms or phenyl-substituted alkyl of 1-20 carbon atoms and X denotes a halogen atom with carbon monoxide and a primary or secondary alcohol, in the presence of a carbonyl derivative of iron, cobalt or nickel as carbonylation catalyst and calcium hydroxide, at a temperature greater than or equal to 90° C. and less than or equal to 130° C.

2. The process of claim 1, wherein, R$_1$ denotes a hydrogen atom or a lower alkyl radical.

3. The process of claim 1, wherein R denotes a phenylalkyl radical.

4. The process of claim 1, wherein the secondary alcohol is isopropanol.

5. The process of claim 1, wherein the amount of the primary or secondary alcohol is at least about one mole per mole of organic halide.

6. The process of claim 1, wherein the amount of calcium hydroxide is about one mole per one mole of organic halide.

7. The process of claim 1, wherein the catalyst is selected from the group consisting of dicobalt octacarbonyl and alkali metal or alkaline earth metal tetracarbonylcobaltates(1).

8. The process of claim 1, wherein the amount of catalyst, expressed as gram-atoms of metal per mole of said organic halide, ranges from about 0.0001:1 to 1:1.

9. The process of claim 8, wherein the amount of catalyst, expressed as gram-atoms of metal per mole of said organic halide, ranges from about 0.001:1 to 0.4:1.

10. The process of claim 1, wherein the step of reacting is performed in the presence of a dissolving intermediary which is inert under the conditions of the reaction.

11. The process of claim 1, wherein the reaction is performed in water or an organic solvent selected from the group consisting of tertiary alcohols and ethers, and mixtures thereof with water.

12. The process of claim 11, wherein the solvent is t-butanol.

13. The process of claim 1, wherein the pressure of carbon monoxide at which the reaction is performed ranges from about 1 to 200 bars.

* * * * *

UNITED STATES PATENT AND TRADEMARK OFFICE
CERTIFICATE OF CORRECTION

PATENT NO. : 4,981,619
DATED : January 01, 1991
INVENTOR(S) : Bernard Besson

It is certified that error appears in the above-identified patent and that said Letters Patent is hereby corrected as shown below:

Title page, item [73] Assignee: change, "Rhone Poulenc Specialities Chimiques" to --Rhone-Poulenc Specialities Chimiques--.

Claim 1, Column 9, Line 15, change "setup" to --step--;

Claim 2, Column 9, Line 32, after "wherein" delete " , ";

Claim 7, Column 10, Line 14, change " (1) " to -- (1-) --.

Signed and Sealed this

Twentieth Day of April, 1993

Attest:

MICHAEL K. KIRK

*Attesting Officer*  *Acting Commissioner of Patents and Trademarks*